United States Patent
Greenberg et al.

(10) Patent No.: US 8,150,534 B2
(45) Date of Patent: *Apr. 3, 2012

(54) ELECTRODE ARRAY FOR EVEN NEURAL PRESSURE

(75) Inventors: Robert J. Greenberg, Los Angeles, CA (US); Mark S. Humayun, Glendale, CA (US); James Singleton Little, Saugus, CA (US); Jordan Matthew Neysmith, Pasadena, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/029,955

(22) Filed: Feb. 17, 2011

(65) Prior Publication Data
US 2011/0144731 A1  Jun. 16, 2011

Related U.S. Application Data

(60) Division of application No. 12/397,974, filed on Mar. 4, 2009, now Pat. No. 7,912,556, which is a continuation-in-part of application No. 12/258,296, filed on Oct. 24, 2008, now Pat. No. 8,014,868.

(60) Provisional application No. 61/033,723, filed on Mar. 4, 2008.

(51) Int. Cl.
A61N 1/00 (2006.01)

(52) U.S. Cl. .................. 607/116
(58) Field of Classification Search ...... 216/6; 606/185; 607/53, 54, 116
See application file for complete search history.

(56) References Cited

U.S. PATENT DOCUMENTS

| | | | |
|---|---|---|---|
| 3,612,061 A * | 10/1971 | Collins et al. ............ | 607/148 |
| 5,109,844 A | 5/1992 | de Juan, Jr. et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,338,322 B2 | 3/2008 | Greenberg | |
| 2006/0247754 A1 | 11/2006 | Greenberg | |
| 2008/0288037 A1 | 11/2008 | Neysmith | |

* cited by examiner

*Primary Examiner* — George Manuel
*Assistant Examiner* — Robert N Wieland
(74) *Attorney, Agent, or Firm* — Scott B. Dunbar; Alessandro Steinfl; Michael Chen

(57) ABSTRACT

An electrode array attached to neural tissue, such as the retina, necessarily has graded pressure exerted on the tissue, with higher pressure near the attachment point. Greater pressure improves contact between the electrodes and neural tissue while too much pressure may damage neural tissue. Hence it is advantageous to obtain equal pressure across the array field. In the present invention multiple and selective attachment points are provided on an electrode array allowing a surgeon to select the attachment points providing the best electrode tissue contact.

14 Claims, 12 Drawing Sheets

ELECTRODE ARRAY FOR EVEN NEURAL PRESSURE

CROSS-REFERENCE TO RELATED APPLICATIONS

This application is a divisional application of 12/397,974, filed Mar. 4, 2009 for Electrode Array for Even Neural Pressure, now U.S. Pat. No. 7,912,556; which is a continuation-in-part of U.S. application Ser. No. 12/258,296, filed Oct. 24, 2008 for Electrode Array for Even Neural Pressure, now U.S. Pat. No. 8,014,868. This application further claims the benefit of U.S. Provisional Application No. 61/033,723, "Attachment Arrangement for a Neural Stimulation Electrode Array", filed Mar. 4, 2008. This application is related to and incorporates by reference US patent publication 20030069603 for "Medical Tack with a Variable Effective Length" of U.S. patent application Ser. No. 09/975,427, filed on Oct. 10, 2001, now abandoned; US patent publication 20080288037 for "Flexible Circuit Electrode Array" of currently pending U.S. patent application Ser. No. 11/934,627, filed on Nov. 2, 2007; and US patent publication 20020111658, for "Implantable retinal electrode array configuration for minimal retinal damage and method of reducing retinal stress" of U.S. patent application Ser. No. 09/783,236, filed on Feb. 13, 2001, now U.S. Pat. No. 7,338,522.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array and means of attachment for a neural stimulation electrode array. The present invention is more specifically directed to a method of obtaining even pressure between an electrode array and a retina by attaching the electrode array at multiple points.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatus to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 μA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

In U.S. Pat. No. 6,743,345 "Method of Metallizing a Substrate" to Christian Belouet et al. a process for metallizing a substrate is disclosed, comprising coating the part with a precursor composite material layer consisting of a polymer matrix doped with photoreducer material dielectric particles; irradiating the surface of the substrate with a light beam emitted by a laser; and immersing the irradiated part in an autocatalytic bath containing metal ions, with deposition of the metal ions in a layer on the irradiated surface, and wherein the dimension of the dielectric particles is less than or equal to 0.5 µm. The process includes three steps. The first step is to coat the substrate part with a precursor composite material layer consisting of a polymer matrix doped with photoreducer material dielectric particles. The second step is to irradiate the surface of the substrate with a light beam emitted by a laser. The third step is to immerse the irradiated part in an autocatalytic bath containing metal ions, with deposition of the metal ions in a layer on the irradiated surface, wherein the dimension of the dielectric particles is less than or equal to 0.5 µm.

In U.S. Pat. No. 5,599,592 "Process for the Metallization of Polymer Materials and Products Thereto Obtained" to Lucien D. Laude a positive metallization process for metallizing a polymer composite piece containing a polymer material and oxide particles is disclosed, the oxide particles being made of one or more oxides, comprising three successive steps. The first step consists of the irradiation of a surface area of a polymer piece to be metallized with a light beam emitted by an excimer laser. The polymer piece is made from a polymer material and oxide particles. The oxide particles are made from one or more oxides. The second step consists of immersing the irradiated polymer piece in at least one autocatalytic bath containing metal ions. The immersion induces the deposit of the metal ions onto the irradiated surface area to form a metal film on the surface area, resulting in the selective metallization of the surface area of the polymer piece. The third step consists of thermally processing the metallized polymer piece to induce diffusion of the deposited metal film into the polymer material of the polymer piece. The disclosure of U.S. Pat. No. 5,599,592 is incorporated herein by reference.

Lucien D. Laude et al. report that excimer lasers are effective tools in engraving ceramics and polymers, changing irreversibly the surface of the irradiated material, and restricting these effects to specific areas of interest. See L. D. Laude, K Kolev, C I. Dicara and C. Dupas-Bruzek "Laser Metallization for Microelectronics for Bio-applications", Proc. of SPIE Vol. 4977 (2003), pp 578-586.

In U.S. Pat. No. 5,935,155 "Visual Prosthesis and Method of Using Same" to Mark S. Humayan et al. it is disclosed a visual prosthesis, comprising means for perceiving a visual image, said means producing a visual signal output in response thereto; retinal tissue stimulation means adapted to be operatively attached to a retina of a user; and wireless visual signal communication means for transmitting said visual signal output to said retinal tissue stimulation means.

In U.S. Pat. No. 6,878,643 "Electronic Unit integrated Into a Flexible Polymer Body" to Peter a. Krulevitch et al. it is disclosed a method of fabricating an electronic apparatus, comprising the steps of providing a silicone layer on a matrix, providing a metal layer on said silicone layer, providing a second layer of silicone on said silicone layer, providing at least one electronic unit connected to said metal layer, and removing said electronic apparatus from said matrix wherein said silicone layer and said second layer of a silicone provide a spherical silicone body.

J. Delbeke et al. demonstrate that silicone rubber biocompatibility is not altered by the metallization method. See V. Cince, M.-A. Thil, C. Veraart, I. M. Colin and J. Delbeke "Biocompatibility of platinum-metallized silicone rubber: in vivo and in vitro evaluation", J. Biomater. Sci. Polymer Edn, Vol. 15, No. 2, pp. 173-188 (2004).

All of these soft polymer arrays approximate the shape of neural tissue, particularly the retina. However, there is a need for an improved means for attaching an electrode array to neural tissue and, thereby, improving the array's ability to conform to the neural tissue.

SUMMARY OF THE INVENTION

An electrode array attached to neural tissue, such as the retina, necessarily has graded pressure exerted on the tissue, with higher pressure near the attachment point. Pressure improves contact between the electrodes and neural tissue while too much pressure may damage neural tissue. Hence it is advantageous to obtain equal pressure across the array field. In the present invention multiple and selective attachment points are provided on an electrode array allowing a surgeon to select the attachment points providing the best electrode tissue contact.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
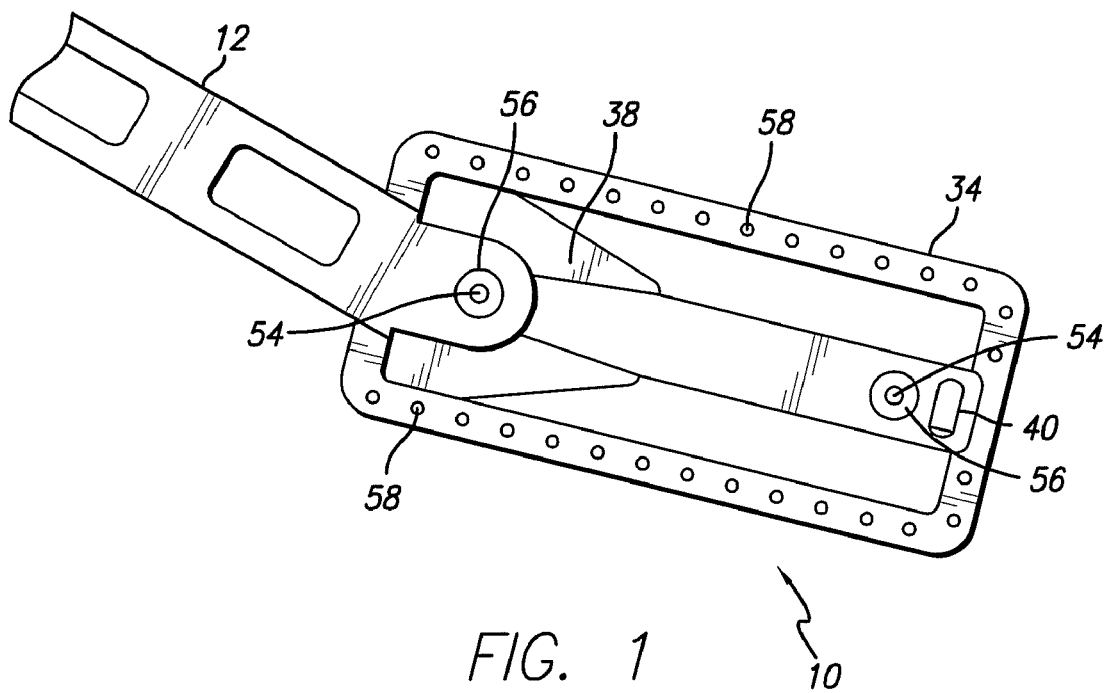
FIG. 1 is a perspective view of the preferred electrode array with two attachment points.

FIG. 1 shows the preferred electrode array. The array 10 is preferably made of metal traces sandwiched between polyimide layers. The array 10 and cable 12 are a single polyimide structure. A relatively hard polymer, such as polyimide, is needed to protect delicate metal traces from breaking. A molded array body 34, preferably silicone, is molded over the polyimide structure. Perforations 58 in the polyimide promote adhesion of the molded array body 34. A backbone structure 38 is molded in silicone across the back of the array 10. Attachment points 54 are provided on either side of the array field to provide even pressure across the array surface. A strain relief 56 is provided around each attachment point 54. The strain relief 56 may be thinner or softer polymer. The strain relief 56 may also include cut out portions. In the preferred embodiment the attachment point 54 is a hole suitable to accept a retinal tack (not shown).

Figure 2:
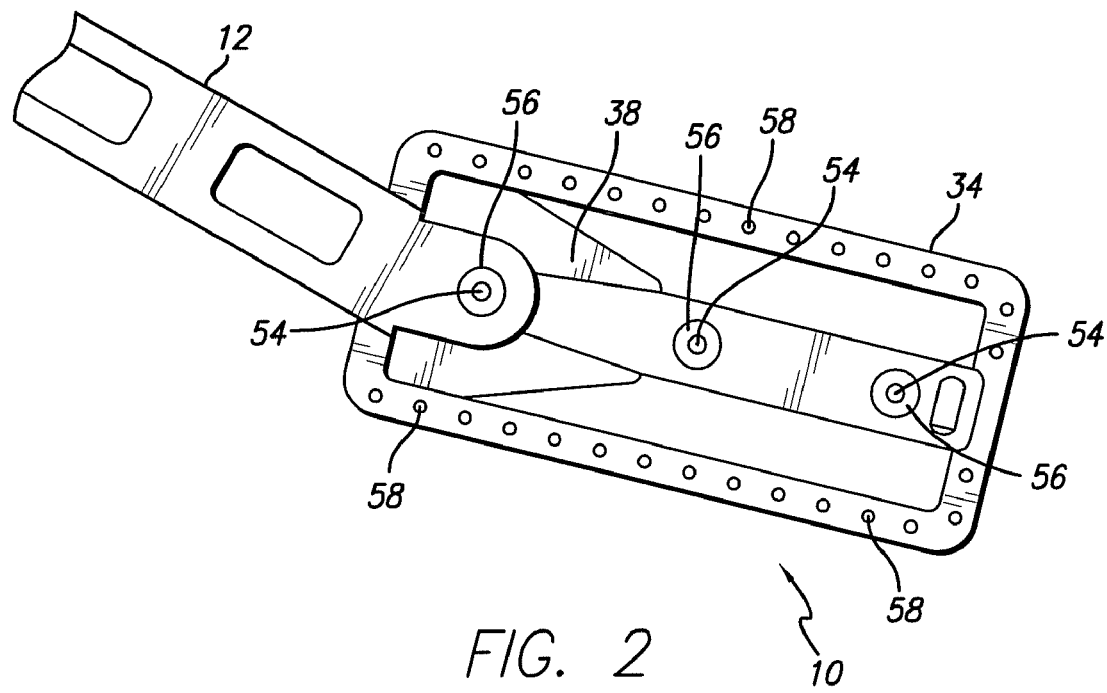
FIG. 2 is a perspective view of the preferred electrode array with three attachment points.

FIG. 2 shows an alternate embodiment with three attachment points 54. The additional attachment point is in the center of the electrode field. With either embodiment, a surgeon may decide at the time of surgery which attachment point to use. The ideal attachment may be determined through impedance. Electrodes with higher impedance have more intimate contact with neural tissue and result in lower a threshold of neural stimulation. Hence, a surgeon may place a tack in the attachment point 54 closest to the cable 12 and measure impedance across the electrode array. If acceptable impedance is found, no additional tacks are required. If not, tacks may be placed where additional force is needed to obtain good electrode contact.

A retinal array is pre-curved to match the approximate curvature of the retina. However, retinas vary considerably in their curvature. In a small eye, the array may not be curved enough. Using only the center attachment point 54 would achieve the best result. In a large eye, the array may be too curved. Using the outer attachment points 54 would achieve the best result.

Figure 3:
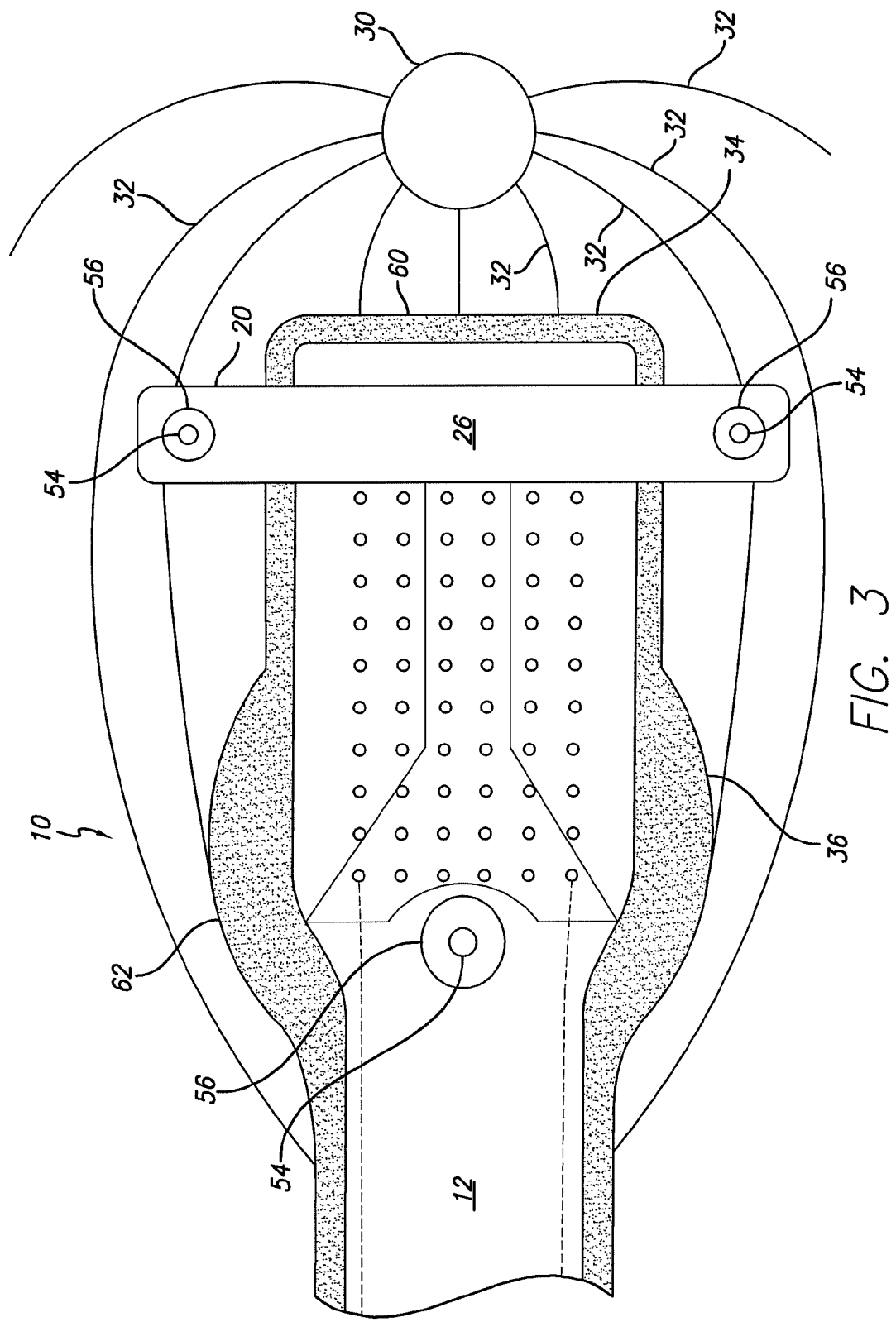
FIG. 3 depicts the electrode array of the preferred embodiment.

FIG. 3 shows the flexible circuit electrode array 10 in another embodiment. A flexible circuit cable 12 connects to the flexible circuit electrode array 10. Further, an attachment point 54 is provided near the heel of the flexible circuit electrode array 10. A retina tack (not shown) is placed through the attachment point 54 to hold the flexible circuit electrode array 10 to the retina or other neural tissue. A stress relief 56 is provided surrounding the attachment point 54. The stress relief 56 may be made of a softer polymer than the flexible circuit, or it may include cutouts or thinning of the polymer to reduce the stress transmitted from the retina tack to the flexible circuit electrode array 10. A molded body 34 covers the flexible circuit electrode array 10, and extends beyond its edges. It may be further advantageous to include wings 36 adjacent to the attachment point 54 to spread any stress of attachment over a larger area of the retina or other neural tissue. There are several ways of forming and bonding the molded body 34. The molded body 34 may be directly bonded through surface activation or indirectly bonded using an adhesive. The molded body 34 may be a molded completely around the electrode array 10 and cable 12.

Preferably the electrode array 10 is constructed from a hard polymer such as polyimide while the molded body 34 is constructed from a softer polymer such as silicone. Traces and electrodes can be laid out on a hard polymer by photolithography and the hard polymer protects the delicate traces. A soft polymer molded body 34 then protects the neural tissue from the hard polymer.

Further a strap 26 may be provided over the array 10 opposite the attachment point 54 near the heel attached at either end by attachment points 54 with retinal tacks. Retinal nerve fibers and blood vessels run orbitally out from the optic nerve. It may be advantageous not to tack between the electrode array 10 and the optic nerve as you may damage the nerve fibers which are stimulated by the electrode array 10. The strap 26 allows the attachment points 54 to be out of the line of the stimulated nerve fibers. The optic nerve 30 is the central access point for both nerve fibers and blood vessels. 32. A tack through either a nerve fiber or blood vessel may cause damage to the area to be stimulated by the electrode array 10.

Figure 4:
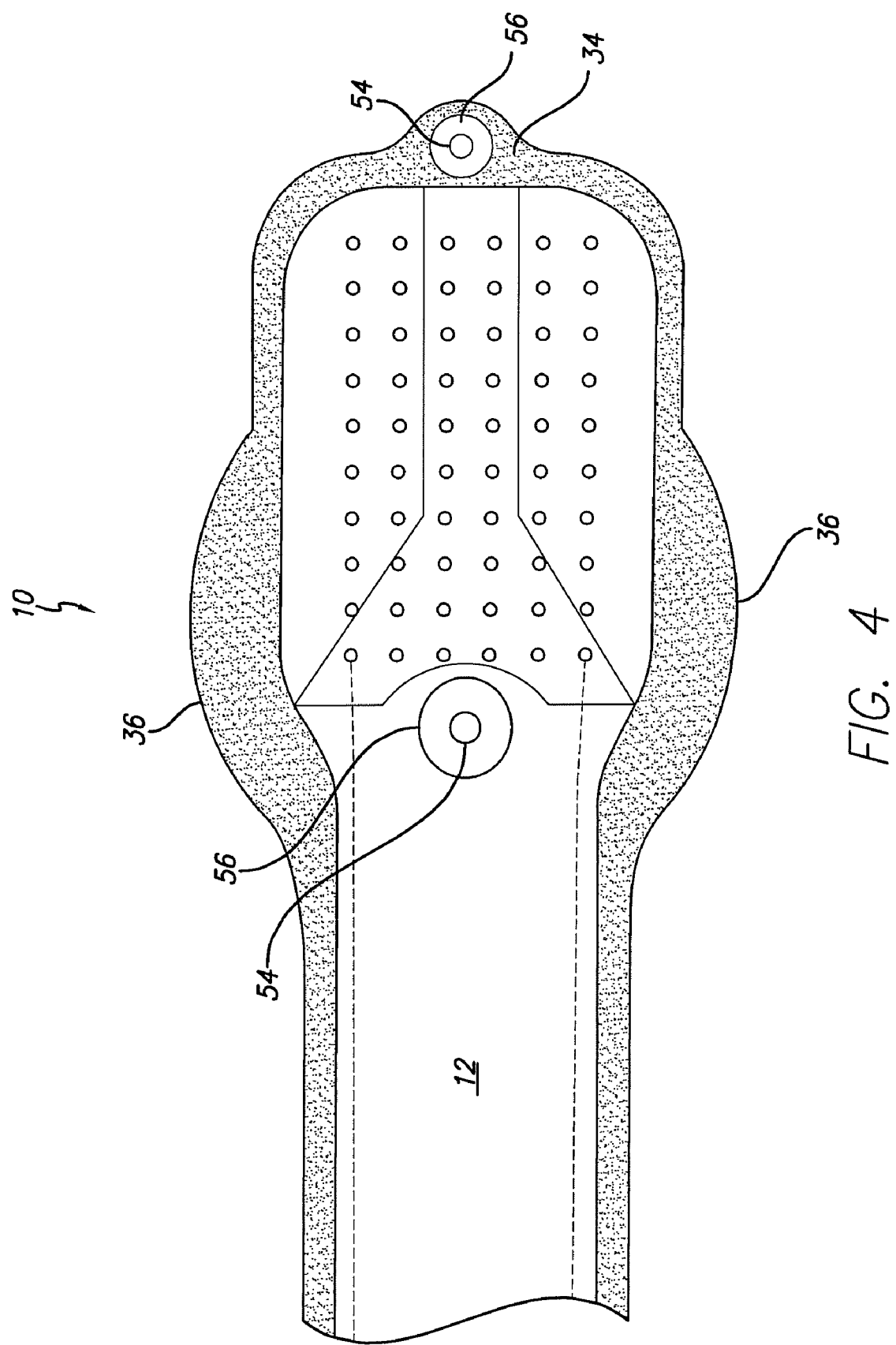
FIG. 4 depicts an electrode array of an alternate two point attachment

Alternatively, FIG. 4 show a central secondary attachment point 54, with a stress relief 56. If the array is not aligned with the nerve fibers a central secondary attachment point may be preferable. FIG. 4 varies from FIG. 2 in that the attachment point 54 near the toe is within the flexible body 34 but outside the array 10. This provides additional stress relief from attachment.

Figure 5:
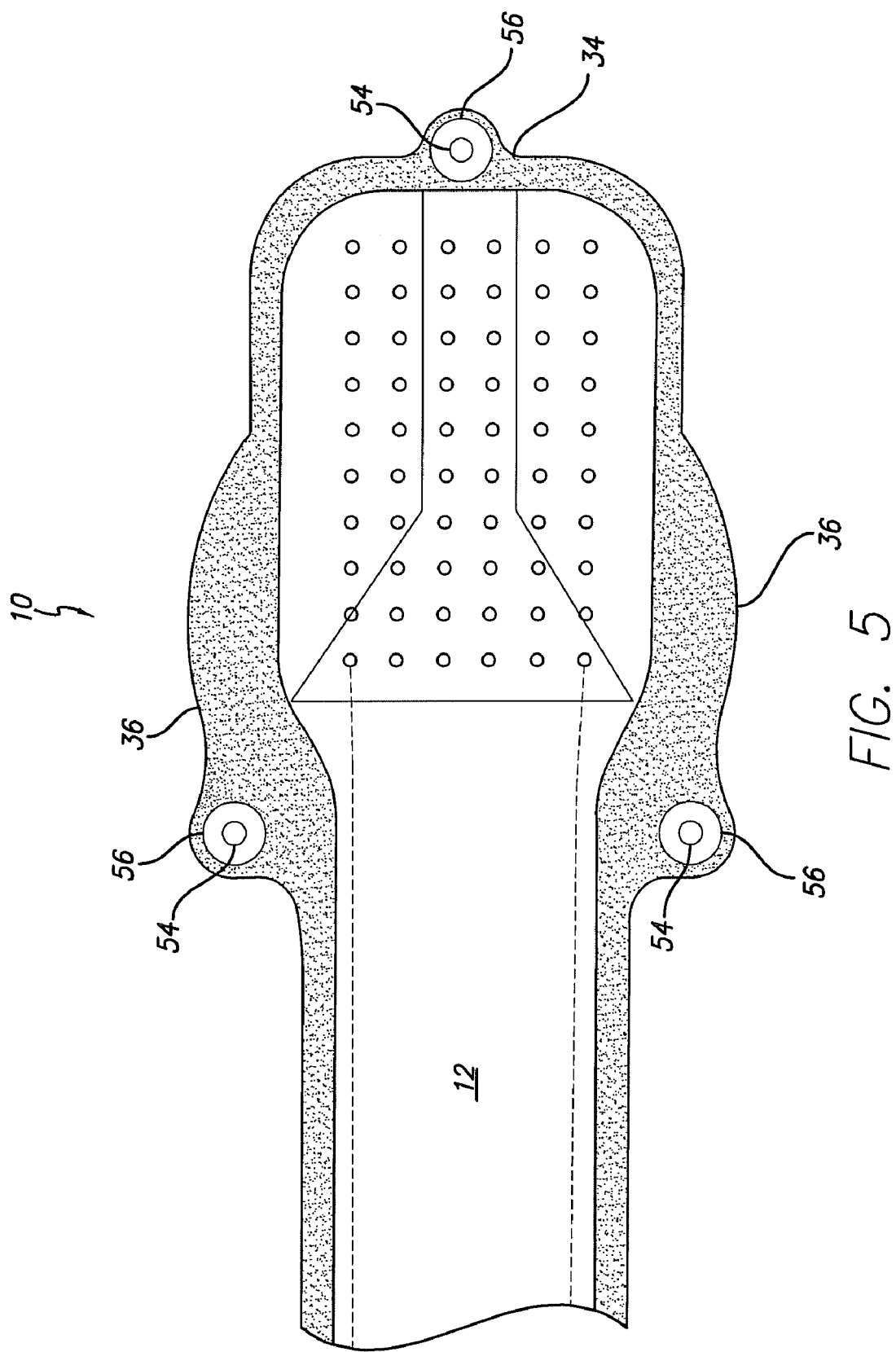
FIG. 5 depicts an electrode array of an alternate three point attachment.

FIG. 5 shows another alternate embodiment. It this case the array may be place in the preferred orientation or an opposite orientation, with the cable passing over the optic nerve. The attachment points 54 includes stress reliefs 56. Attachment points 54, with stress relief 56, are included in the wings 62. An additional advantage of this embodiment is that any rotational torque from the array cable is transmitted to the electrode field portion of the flexible body.

Figure 6:
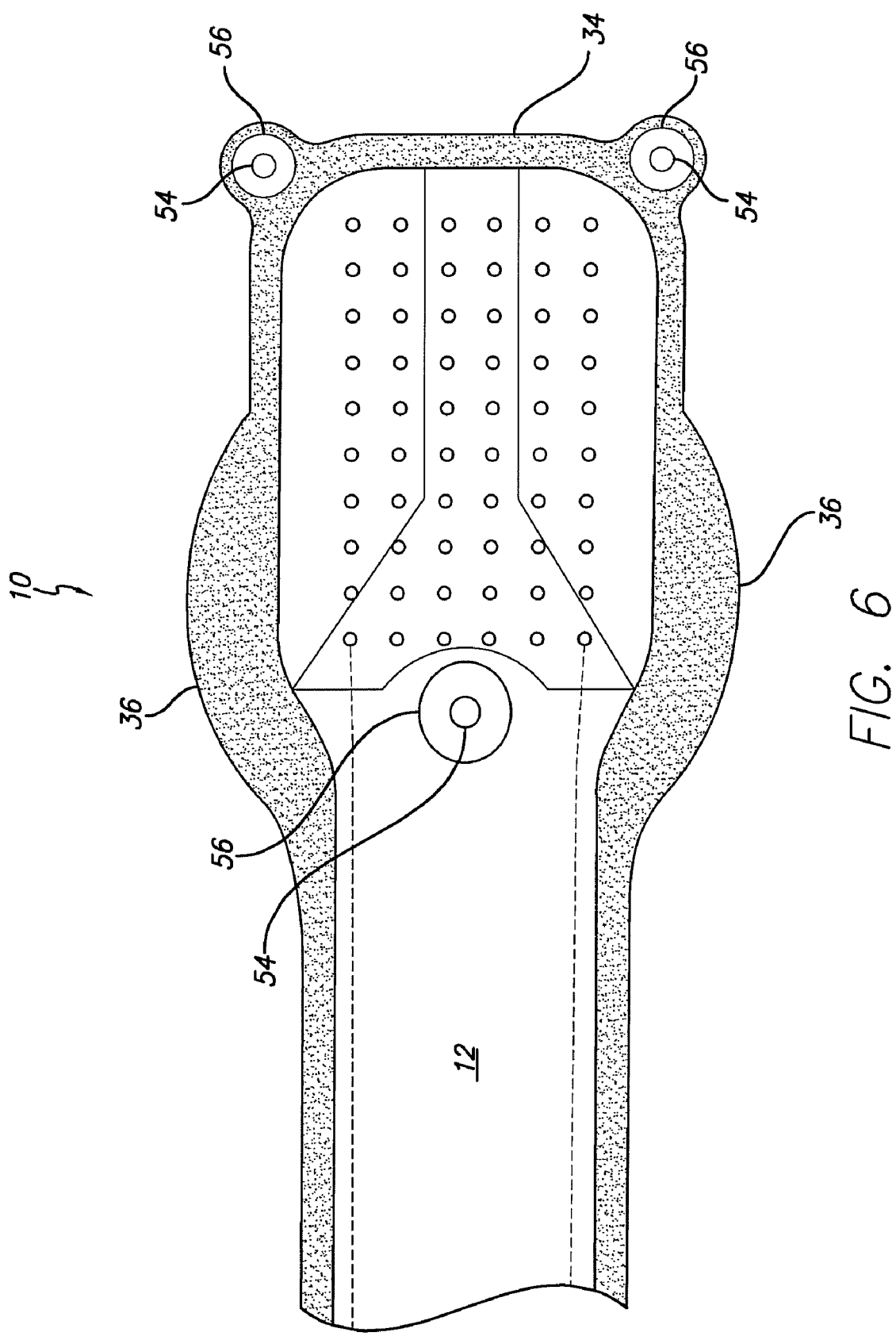
FIG. 6 depicts an electrode array with another alternate three point attachment.

FIG. 6 shows another alternate embodiment similar to the embodiment shown in FIG. 3, but with attachment points 54 integral to the array body rather than on a separate strap. As with the embodiment of FIG. 3, the attachment points are outside of the area of the nerve fibers and blood vessels supplying the areas to be stimulated.

Figure 7:
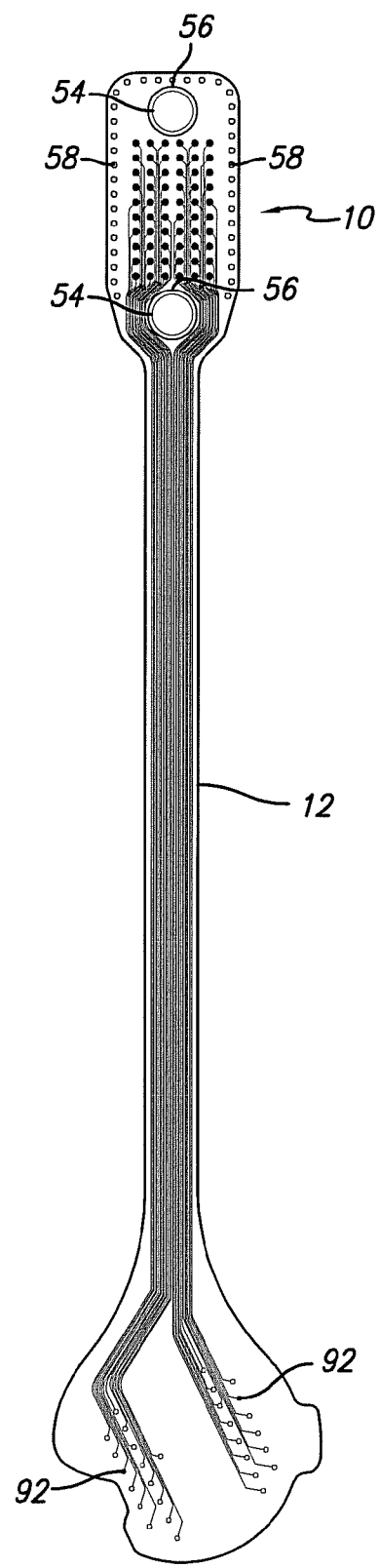
FIG. 7 shows the whole flexible polymer array with the bond pad and the traces with holes at the edge of the electrode array.

FIG. 7 shows the preferred electrode array for a visual prosthesis. The structure is a single polyimide sandwich with metal traces. The array 10 is at one end. Bond pads 92 are at the other end and the cable 12 is in the middle. One trace connects each electrode with a bond pad. The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrode to improve contact with neural tissue, and at the bond pad to improve contact with the package. This can be accomplished through any of the above methods or electroplating. Then, the top layer of polymer is applied over the metal. Openings in the top layer for electrical contact to the electronics package 14 and the electrodes may be accomplished by laser ablation or reactive ion etching (RIE) or photolithography and wet etch. Making the electrode openings in the top layer smaller than the electrodes promotes adhesion by avoiding delamination around the electrode edges.

Figure 8:
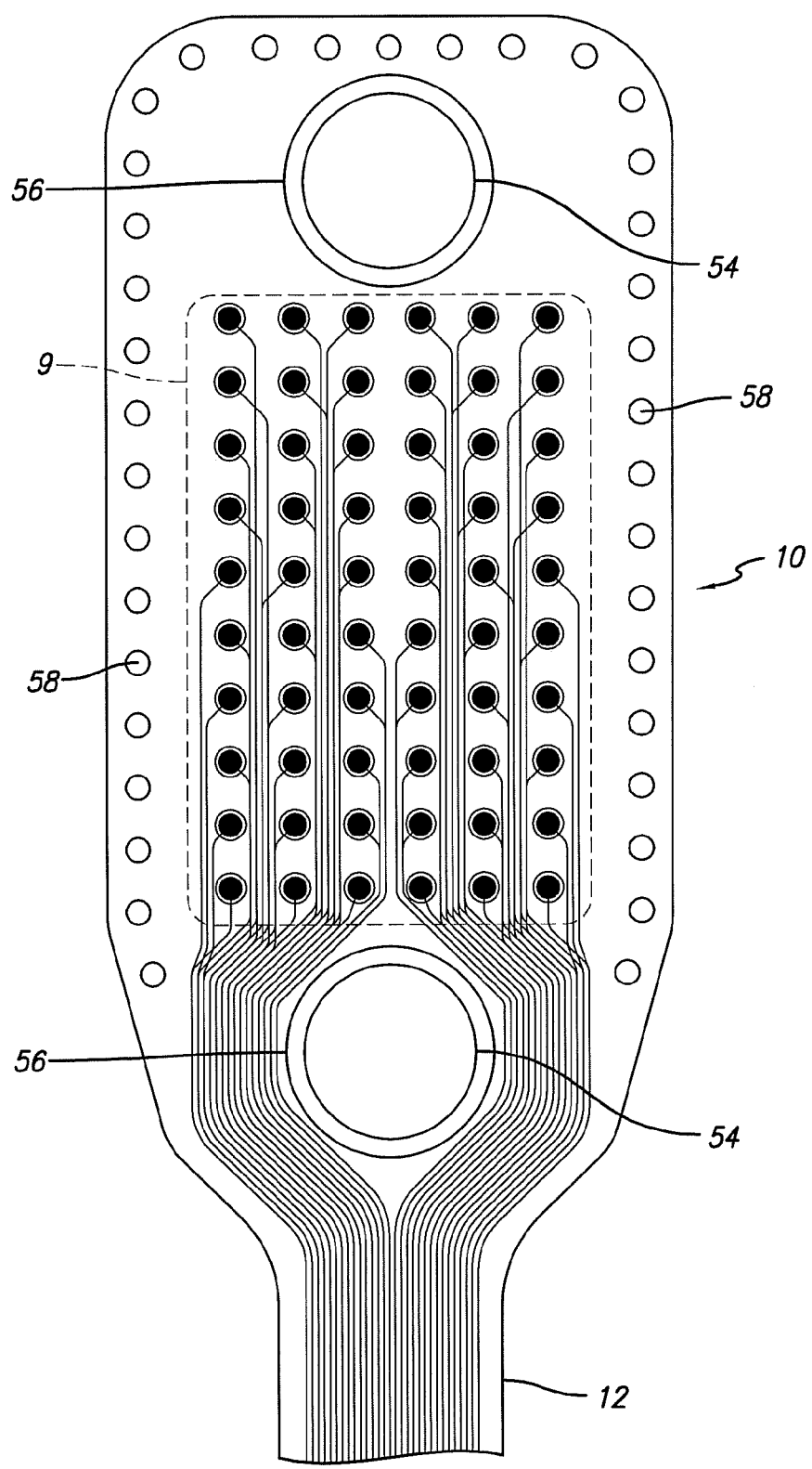
FIG. 8 shows an enlarged view of the electrode array with holes at the edge of the polyimide to improve silicone adhesion.

FIG. 8 is an enlarged view of the electrode array 10. Traces must be routed around the attachment point 54 and stress relief 56. The electrode field 9, shown by a dotted line, is that portion of the electrode array having electrodes and stimulating neural tissue.

Figure 9:
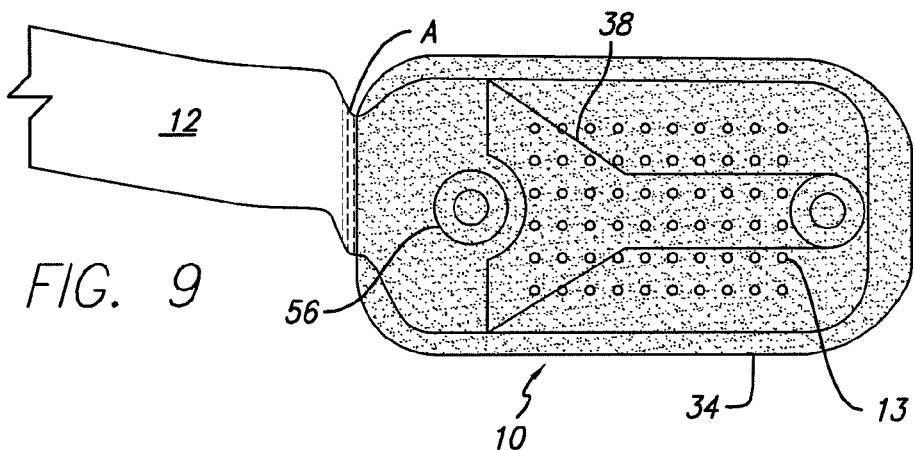
FIG. 9 depicts the top view of the flexible circuit array being enveloped within an insulating material.

FIG. 9 depicts the top view of the flexible circuit array 10 being enveloped within a molded body 34. The electrode array 10 is encased within the oval-shaped molded body 34, a plurality of electrodes 13 made of a conductive material, such as platinum or one of its alloys, but that can be made of any conductive biocompatible material such as iridium, iridium oxide or titanium nitride. The electrode array 10 is enveloped within a molded body 34 that is preferably silicone. "Oval-shaped" electrode array body means that the body may approximate either a square or a rectangle shape, but where the corners are rounded. This shape of an electrode array is described in the U.S. Patent Application No. 20020111658, entitled "Implantable retinal electrode array configuration for minimal retinal damage and method of reducing retinal stress" and No. 20020188282, entitled "Implantable drug delivery device" to Robert J. Greenberg et al., the disclosures of both are incorporated herein by reference.

The molded body 34 is made of a soft material that is compatible with the electrode array 10. In a preferred embodiment the molded body 34 made of silicone having hardness of about 50 or less on the Shore A scale as measured with a durometer. In an alternate embodiment the hardness is about 25 or less on the Shore A scale as measured with a durometer.

Figure 10:
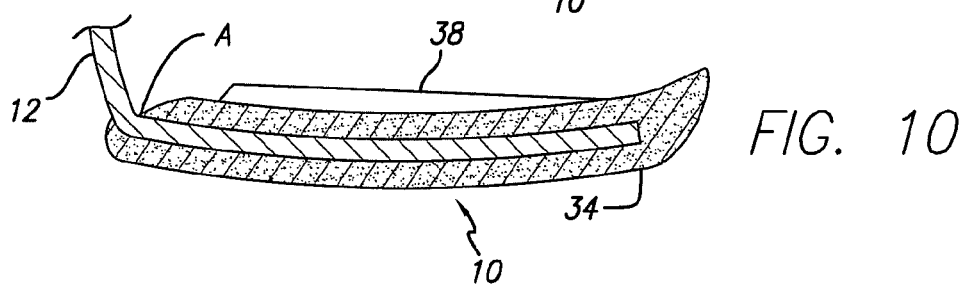
FIG. 10 depicts a cross-sectional view of the flexible circuit array being enveloped within an insulating material.

FIG. 10 depicts a cross-sectional view of the flexible circuit array 10 being enveloped within the molded body 34. It shows how the edges of the molded body 34 are lifted off due to the contracted radius at the edges. The electrode array 10 preferably also contains a fold A between the cable 12 and the electrode array 10. The angle of the fold A secures a relief of the implanted material.

Figure 11:
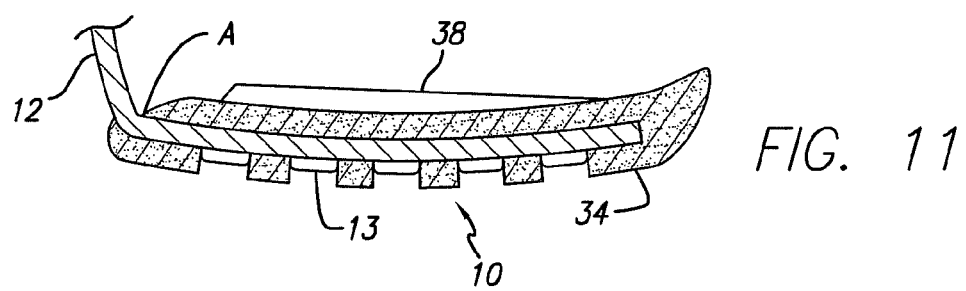
FIG. 11 depicts a cross-sectional view of the flexible circuit array being enveloped within an insulating material with open electrodes and the material between the electrodes.

FIG. 11 depicts a cross-sectional view of the flexible circuit array 10 being enveloped within a molded body 34 with open electrodes 13 and the molded body 34 between the electrodes 13.

Figure 12:
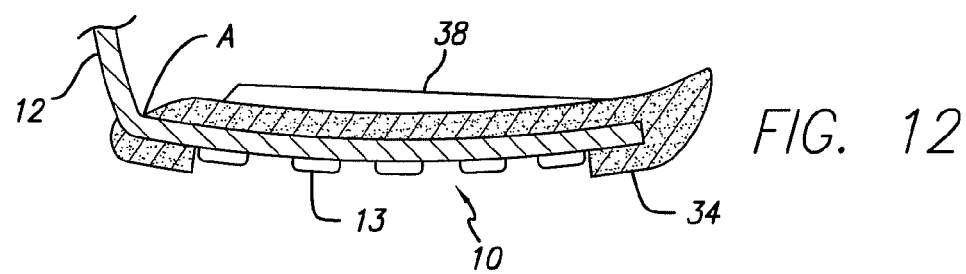
FIG. 12 depicts a cross-sectional view of the flexible circuit array being enveloped within an insulating material with open electrodes.

FIG. 12 depicts a cross-sectional view of the flexible circuit array 10 being enveloped within the molded body 34 with open electrodes 13. This is another embodiment wherein the electrodes 13 are not separated by the molded body 34. This may allow closer contact with the neural tissue.

Figure 13:
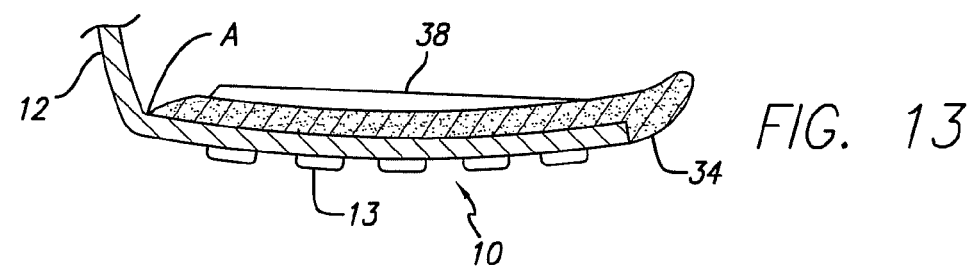
FIG. 13 depicts a cross-sectional view of the flexible circuit array being enveloped within an insulating material with electrodes on the surface of the material.
Figure 14:
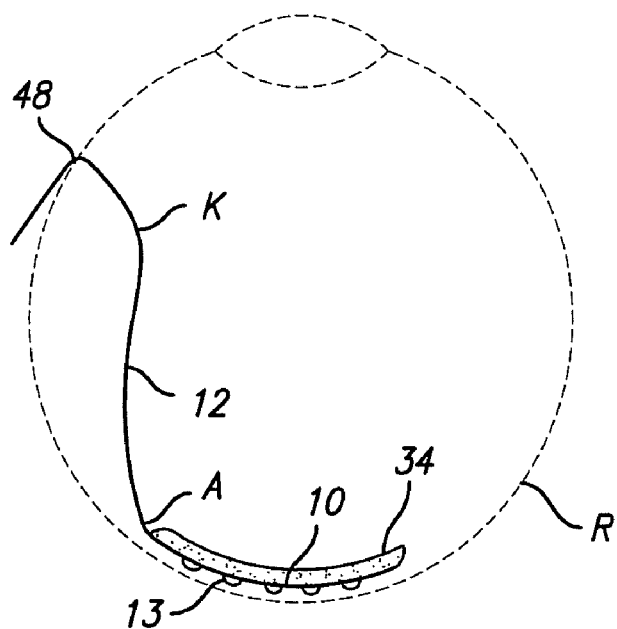
FIG. 14 depicts a cross-sectional view of the flexible circuit array being enveloped within an insulating material with electrodes on the surface of the material insight the eye with an angle in the fold of the flexible circuit cable and a fold between the circuit electrode array and the flexible circuit cable.

FIG. 13 depicts a cross-sectional view of the flexible circuit array 10 being enveloped within the molded body 34 with electrodes 13 on the surface of the molded body 34. This is a further embodiment with the electrode 13 on the surface of the molded body, preferably silicone. The embodiments shown in FIG. 14 depicts a cross-sectional view of the flexible circuit array 10 being enveloped within the molded body 34 with electrodes 13 on the surface of the molded body 34 insight the eye with an angle K in the fold of the flexible circuit cable 12 and a fold A between the circuit electrode array 10 and the flexible circuit cable 12. The molded body 34 and electrode array body 10 are in intimate contact with retina R. The surface of electrode array body 10 in contact with retina R is a curved surface with a matched radius compared to the spherical curvature of retina R to minimize pressure concentrations therein. Further, the decreasing radius of spherical curvature of the molded body 34 near its edge forms edge relief that causes the edges of the molded body 34 to lift off the surface of retina R eliminating pressure concentrations at the edges. The edge of molded body 34 is rounded to reduce pressure and cutting of retina R.

Figure 15:
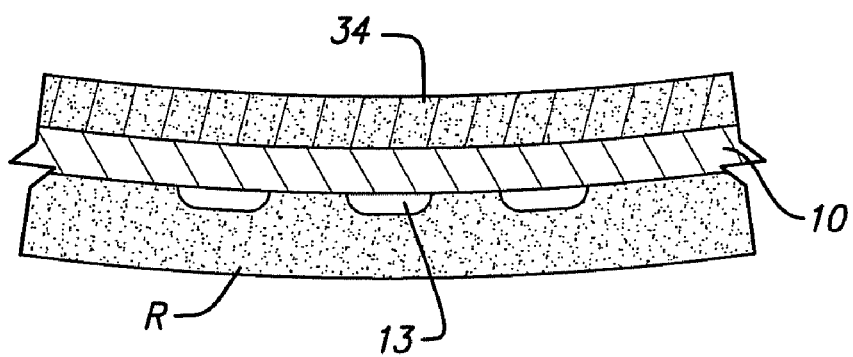
FIG. 15 depicts a side view of the enlarged portion of the flexible circuit array being enveloped within an insulating material with electrodes on the surface of the material in the eye and contacting the retina.

FIG. 15 shows a part of the FIG. 14 enlarged showing the electrode array 10 and the electrodes 13 enveloped by the molded body 34, preferably silicone in intimate contact with the retina R.

The electrode array 10 embedded in or enveloped by the molded body 34 can be preferably produced through curing the silicone in a mold around the polyimide array 10. The molded body 34 has a shape with a decreasing radius at the edges so that the edges of the molded body 34 lift off from the retina R.

Figure 16:
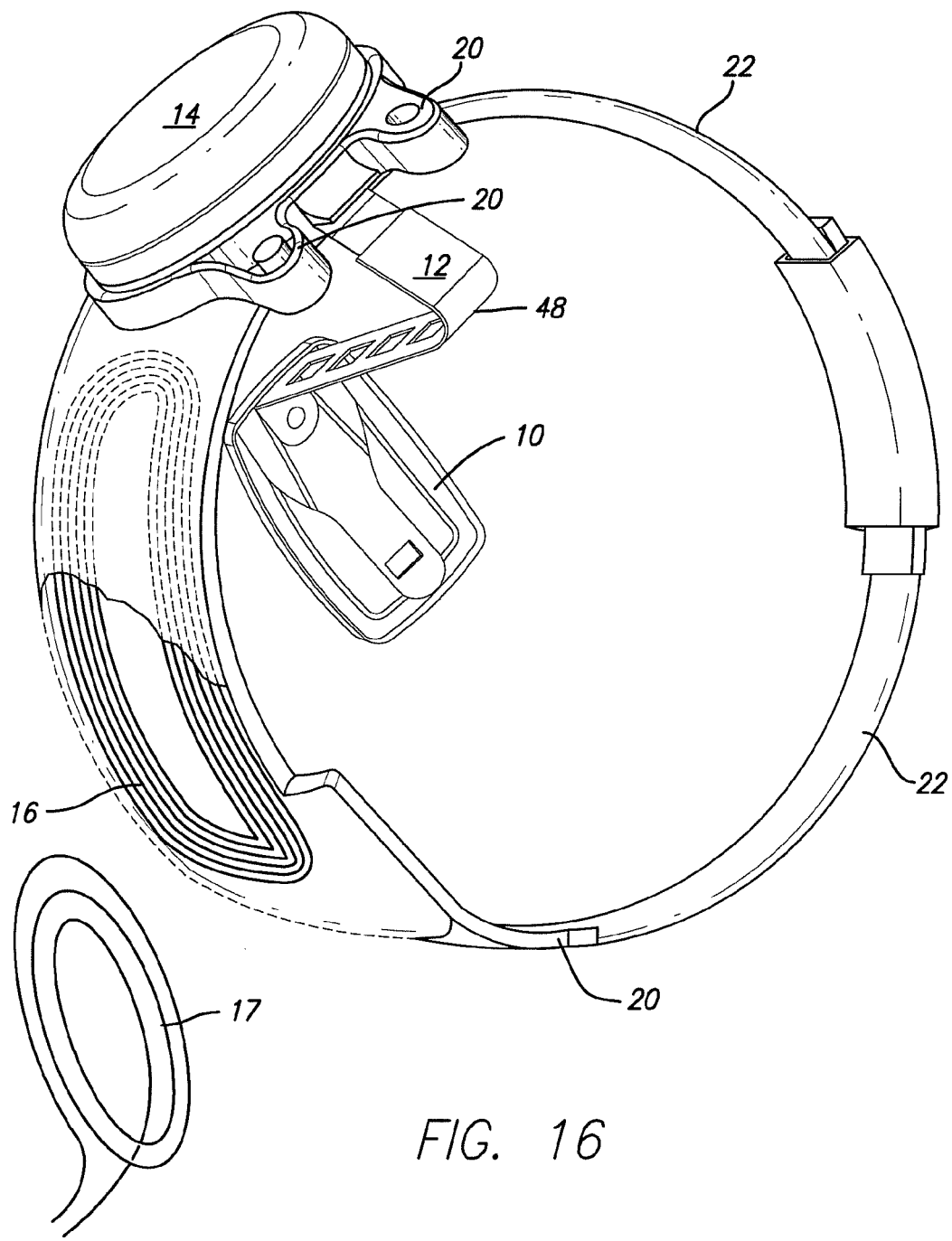
FIG. 16 is a perspective view of the implanted portion of the preferred retinal prosthesis.

FIG. 16 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 17:
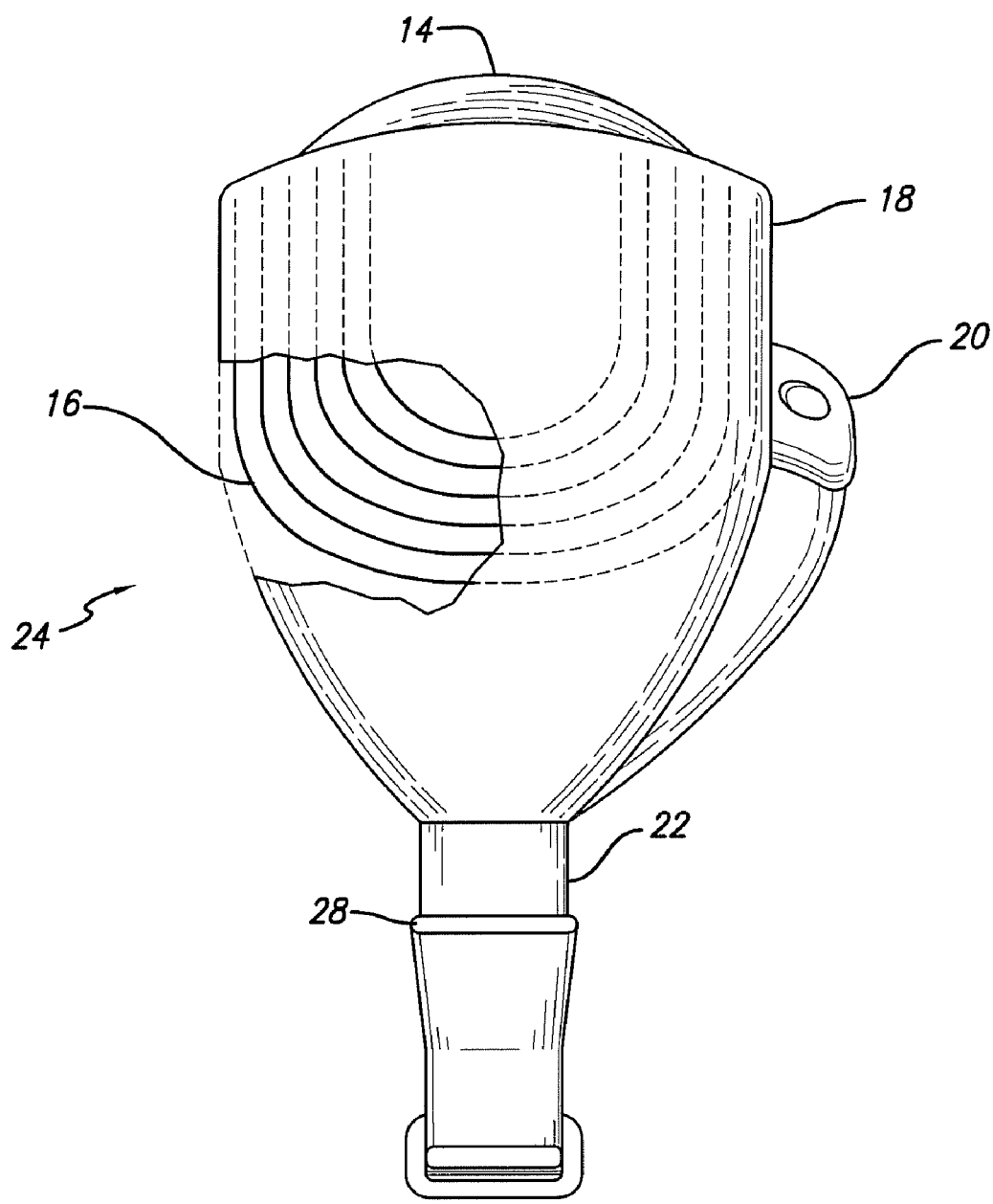
FIG. 17 is a side view of the implanted portion of the preferred retinal prosthesis showing the fan tail in more detail.

FIG. 17 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 18:
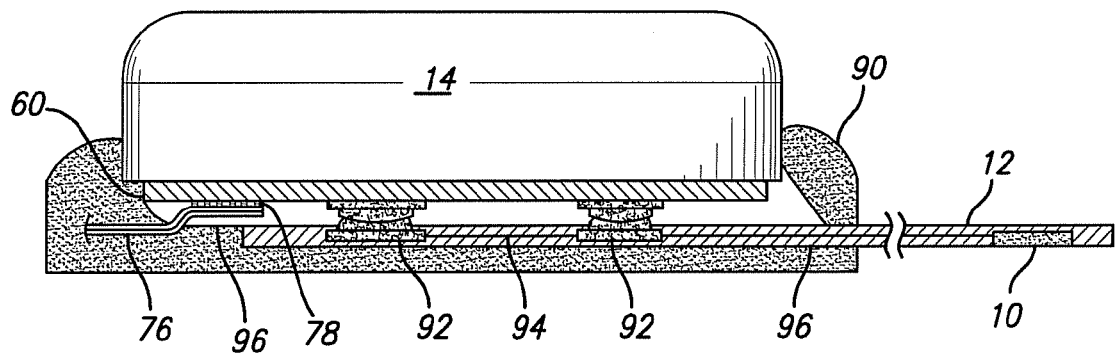
FIG. 18 is a view of the completed package attached to an electrode array.

Referring to FIG. 18, the flexible circuit 1, includes platinum conductors 94 insulated from each other and the external environment by a biocompatible dielectric polymer 96, preferably polyimide. One end of the array contains exposed electrode sites that are placed in close proximity to the retinal surface 10. The other end contains bond pads 92 that permit electrical connection to the electronics package 14. The electronic package 14 is attached to the flexible circuit 1 using a flip-chip bumping process, and epoxy underfilled. In the flip-chip bumping process, bumps containing conductive adhesive placed on bond pads 92 and bumps containing conductive adhesive placed on the electronic package 14 are aligned and melted to build a conductive connection between the bond pads 92 and the electronic package 14. Leads 76 for the secondary inductive coil 16 are attached to gold pads 78 on the ceramic substrate 60 using thermal compression bonding, and are then covered in epoxy. The electrode array cable 12 is laser welded to the assembly junction and underfilled with epoxy. The junction of the secondary inductive coil 16, array 1, and electronic package 14 are encapsulated with a silicone overmold 90 that connects them together mechanically. When assembled, the hermetic electronics package 14 sits about 3 mm away from the end of the secondary inductive coil.

Since the implant device is implanted just under the conjunctiva it is possible to irritate or even erode through the conjunctiva. Eroding through the conjunctiva leaves the body open to infection. We can do several things to lessen the likelihood of conjunctiva irritation or erosion. First, it is important to keep the over all thickness of the implant to a minimum. Even though it is advantageous to mount both the electronics package 14 and the secondary inductive coil 16 on the lateral side of the sclera, the electronics package 14 is mounted higher than, but not covering, the secondary inductive coil 16. In other words the thickness of the secondary inductive coil 16 and electronics package should not be cumulative.

It is also advantageous to place protective material between the implant device and the conjunctiva. This is particularly important at the scleratomy, where the thin film electrode array cable 12 penetrates the sclera. The thin film electrode array cable 12 must penetrate the sclera through the pars plana, not the retina. The scleratomy is, therefore, the point where the device comes closest to the conjunctiva. The protective material can be provided as a flap attached to the implant device or a separate piece placed by the surgeon at the time of implantation. Further material over the scleratomy will promote healing and sealing of the scleratomy. Suitable materials include DACRON®, TEFLON®, GORETEX® (ePTFE), TUTOPLAST® (sterilized sclera), MERSILENE® (polyester) or silicone.

Figure 19:
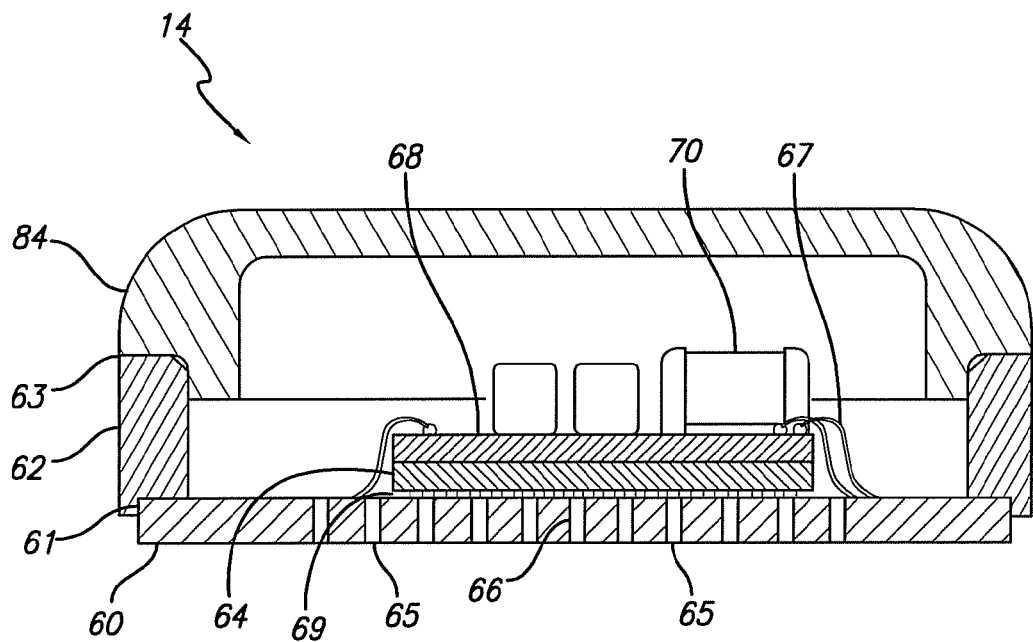
FIG. 19 is a cross-section of the package.

Referring to FIG. 19, the package 14 contains a ceramic substrate 60, with metalized vias 65 and thin-film metallization 66. The package 14 contains a metal case wall 62 which is connected to the ceramic substrate 60 by braze joint 61. On the ceramic substrate 60 an underfill 69 is applied. On the underfill 69 an integrated circuit chip 64 is positioned. On the integrated circuit chip 64 a ceramic hybrid substrate 68 is positioned. On the ceramic hybrid substrate 68 passives 70 are placed. Wirebonds 67 are leading from the ceramic substrate 60 to the ceramic hybrid substrate 68. A metal lid 84 is connected to the metal case wall 62 by laser welded joint 63 whereby the package 14 is sealed.

Accordingly, what has been shown is an improved method making a neural electrode array and improved method of stimulating neural tissue. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. An electrode array for neural stimulation comprising:
   an electrode array for stimulating neural tissue within an array body having a heel proximate to a supply cable and a toe opposite said heel;
   an attachment point within said array body; and
   a strap having a plurality of attachment points suitable to locate said array body proximate to neural tissue,
   wherein said electrode array is suitable to contact retinal tissue to electrically induce artificial vision.

2. The electrode array according to claim 1, wherein said attachment point within said array body is within said heel and said strap is suitable to locate said toe.

3. The electrode array according to claim 1, wherein said attachment point within said array body is within said toe and said strap is suitable to locate said heel.

4. The electrode array according to claim 1, further comprising a stress relief between at least one of said attachment points and said array body.

5. The electrode array according to claim 4, wherein said stress relief is a soft polymer.

6. The electrode array according to claim 1, wherein said electrode array body comprises a soft polymer formed over a hard polymer.

7. The electrode array according to claim 6, wherein said attachments points are formed in said soft polymer.

8. The electrode array according to claim 1, further comprising a backbone structure for controlling the stiffness of the array body.

9. A flexible circuit electrode array comprising:
   a polymer base layer;
   metal traces deposited on said polymer base layer;
   a polymer top layer deposited on said polymer base layer and said metal traces forming a supply cable and electrode body, the electrode body including electrodes suitable to stimulate neural tissue in an electrode field, and having a heel proximate to said supply cable and a toe opposite said heel;

a partial or entire coating of the base and top layer by a soft polymer; and an attachment point within said array body; and a strap having a plurality of attachment points suitable to locate said array body proximate to neural tissue, wherein said electrode array is suitable to contact retinal tissue to electrically induce artificial vision.

10. The electrode according to claim 9, wherein said attachment point within said array body is within said heel and said strap is suitable to locate said toe.

11. The electrode array according to claim 9, wherein said attachment point within said array body is within said toe and said strap is suitable to locate said heel.

12. The electrode array according to claim 9, further comprising a stress relief between at least one of said attachment points and said array body.

13. The electrode array according to claim 12, wherein said stress relief is said soft polymer.

14. The electrode array according to claim 9 further comprising a backbone structure for controlling the stiffness of the array body.

* * * * *